United States Patent [19]
Berthiaume

[11] Patent Number: 5,377,690
[45] Date of Patent: Jan. 3, 1995

[54] GUIDEWIRE WITH ROUND FORMING WIRE

[75] Inventor: William A. Berthiaume, Hudson, Mass.

[73] Assignee: C. R. Bard, Inc., Murray Hill, N.J.

[21] Appl. No.: 15,642

[22] Filed: Feb. 9, 1993

[51] Int. Cl.⁶ ............................................. A61B 5/00
[52] U.S. Cl. .................................................... 128/772
[58] Field of Search .................. 128/657, 772; 604/95, 604/280–283

[56] References Cited

U.S. PATENT DOCUMENTS

| | | | |
|---|---|---|---|
| Re. 33,911 | 5/1992 | Samson et al. | 128/772 |
| 3,452,742 | 7/1969 | Muller . | |
| 3,521,620 | 7/1970 | Cook | 128/2.05 |
| 3,528,406 | 9/1970 | Jeckel et al. | 128/2.05 |
| 3,552,384 | 1/1971 | Pierie et al. | 128/2.05 |
| 3,631,848 | 1/1972 | Muller | 128/2.05 R |
| 3,749,086 | 7/1973 | Kline et al. | 128/2 M |
| 3,757,768 | 9/1973 | Kline | 128/2 M |
| 3,789,841 | 2/1974 | Antoshkiw | 128/2.05 R |
| 3,906,938 | 9/1975 | Fleischhacker | 128/2 M |
| 4,003,369 | 1/1977 | Heilman et al. | 128/2 M |
| 4,020,829 | 5/1977 | Willson et al. | 128/2 M |
| 4,080,706 | 3/1978 | Heliman et al. | 29/173 |
| 4,215,703 | 8/1980 | Willson | 128/172 |
| 4,456,017 | 6/1984 | Miles | 128/772 |
| 4,538,622 | 9/1985 | Samson et al. | 128/772 |
| 4,548,206 | 10/1985 | Osborne | 128/772 |
| 4,554,929 | 11/1985 | Samson et al. | 128/772 |
| 4,619,274 | 10/1986 | Morrison | 128/772 |
| 4,721,117 | 1/1988 | Mar et al. | 128/772 |
| 4,724,846 | 2/1988 | Evans, III | 128/772 |
| 4,748,982 | 6/1988 | Horzewski et al. | 128/344 |
| 4,748,986 | 6/1988 | Morrison et al. | 128/772 |
| 4,757,827 | 7/1988 | Buchbinder et al. | 128/772 |
| 4,798,598 | 1/1989 | Bonello et al. | 604/280 |
| 4,811,743 | 3/1989 | Stevens | 128/772 |
| 4,813,434 | 3/1989 | Buchbinder et al. | 128/772 |
| 4,815,478 | 3/1989 | Buchbinder et al. | 128/772 |
| 4,832,047 | 5/1989 | Sepetka et al. | 128/772 |
| 4,846,186 | 7/1989 | Box et al. | 128/657 |
| 4,846,193 | 7/1989 | Tremulis et al. | 128/772 |
| 4,854,330 | 8/1989 | Evans, III et al. | 128/772 |
| 4,867,173 | 9/1989 | Leoni | 128/772 |
| 4,873,983 | 10/1989 | Winters | 128/657 |
| 4,884,579 | 12/1989 | Engelson | 128/772 |
| 4,886,067 | 12/1989 | Palermo | 128/657 |
| 4,917,104 | 4/1990 | Rebell | 128/772 |
| 4,917,666 | 4/1990 | Solar et al. | 604/95 |
| 4,921,482 | 5/1990 | Hammerslag et al. | 604/95 |
| 4,922,924 | 5/1990 | Gambale et al. | 128/772 |
| 4,925,445 | 5/1990 | Sakamoto et al. | 604/95 |
| 4,940,062 | 7/1990 | Hampton et al. | 128/772 |
| 4,953,553 | 9/1990 | Tremulis | 128/637 |
| 4,964,409 | 10/1990 | Tremulis | 128/657 |
| 4,966,163 | 10/1990 | Kraus et al. | 128/772 |
| 4,971,490 | 11/1990 | Hawkins | 128/772 |
| 4,984,581 | 1/1991 | Stice | 128/772 |
| 4,998,916 | 3/1991 | Hammerslag et al. | 604/95 |
| 4,998,917 | 3/1991 | Gaiser et al. | 604/96 |
| 5,037,391 | 8/1991 | Hammerslag et al. | 604/95 |
| 5,040,543 | 8/1991 | Badera et al. | 128/772 |
| 5,055,109 | 10/1991 | Gould et al. | 604/95 |
| 5,060,660 | 10/1991 | Gambale et al. | 128/772 |
| 5,065,769 | 11/1991 | de Toledo | 128/772 |
| 5,067,489 | 11/1991 | Lind | 128/772 |
| 5,069,217 | 12/1991 | Fleischhacker, Jr. | 128/657 |
| 5,095,915 | 3/1992 | Engelson | 128/772 |

FOREIGN PATENT DOCUMENTS 0014424 8/1980 European Pat. Off. .

Primary Examiner—Max Hindenburg
Attorney, Agent, or Firm—Morgan & Finnegan

[57] ABSTRACT

A guidewire including a core wire extending into a lumen of a helical coil and having a proximal end of the helical coil fixedly attached thereto. At least one round forming wire is fixedly attached to a distal region of the core wire and extends through the lumen of the helical coil. A rounded protrusion is provided at a distal end of the helical coil with the round forming wire(s) and the helical coil fixedly attached thereto.

7 Claims, 4 Drawing Sheets

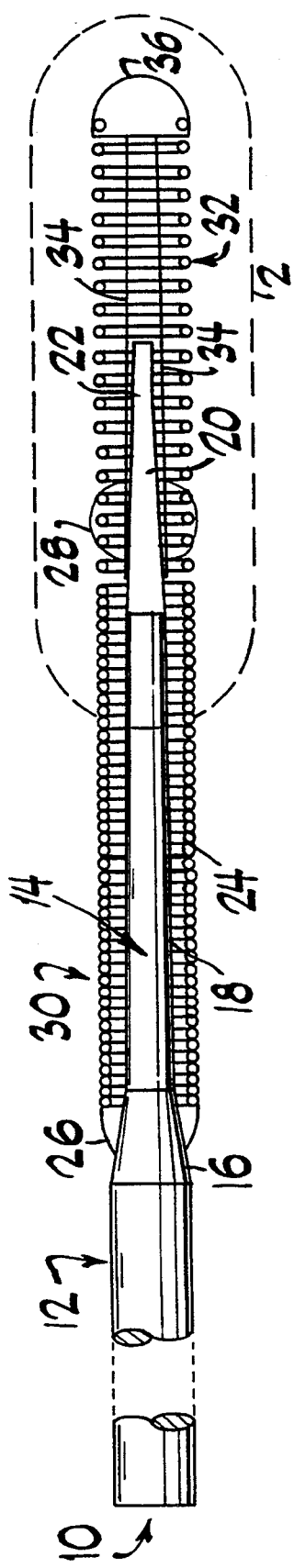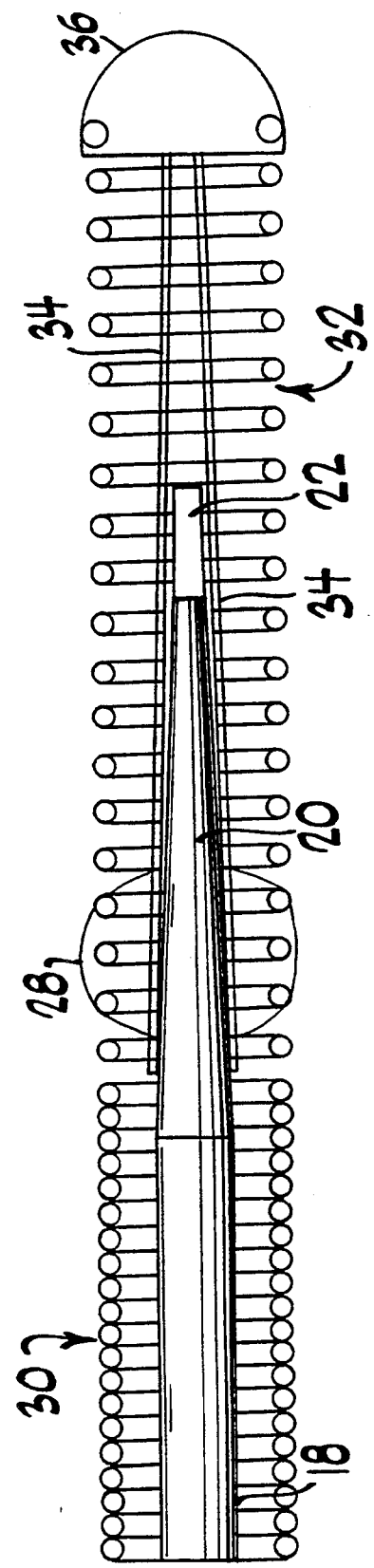
FIG. 1
FIG. 2

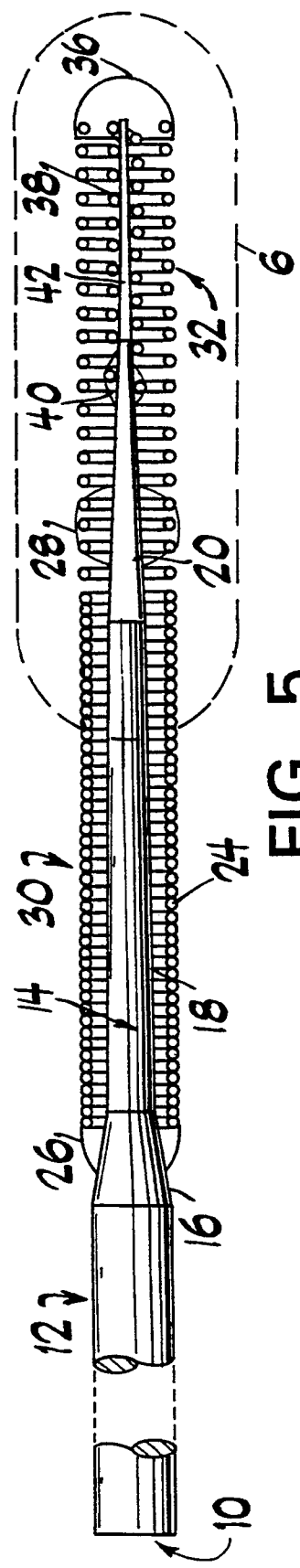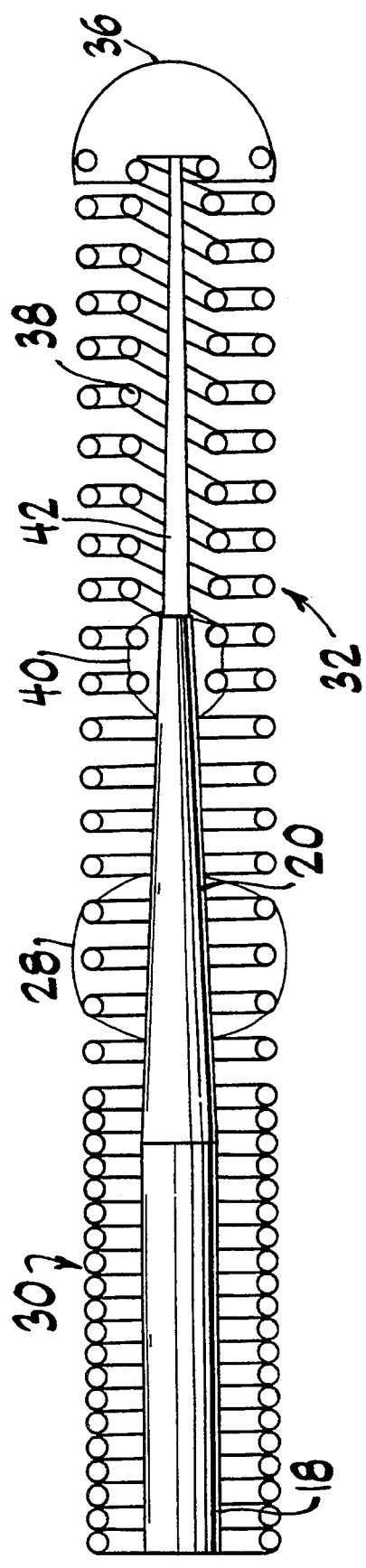

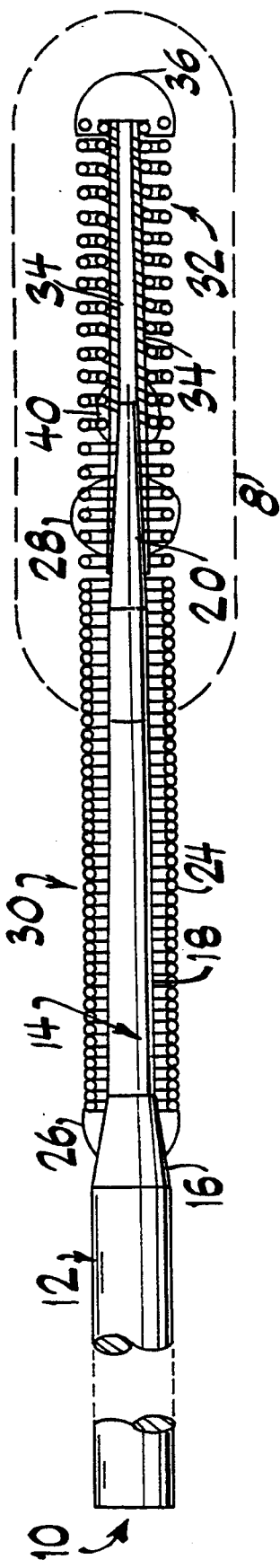
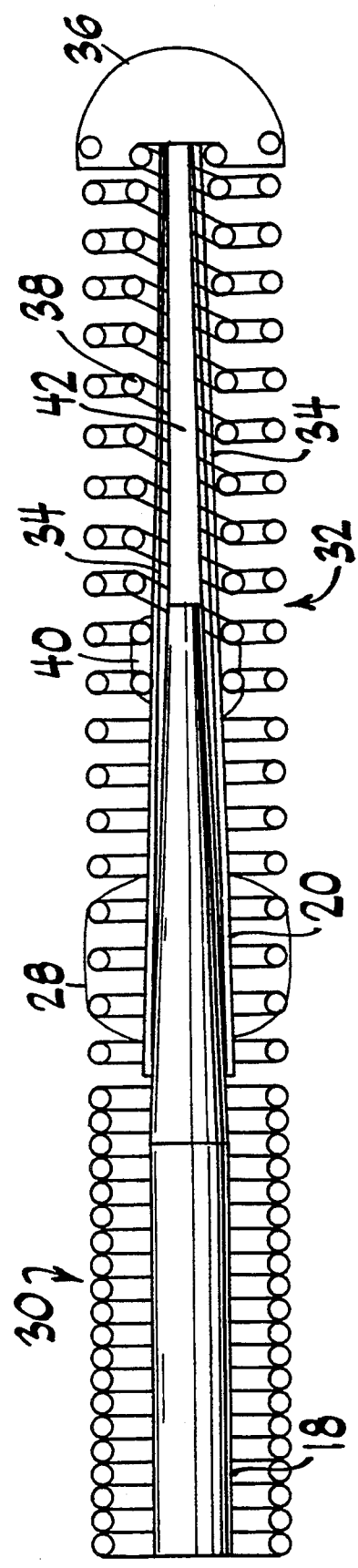
FIG. 7
FIG. 8

GUIDEWIRE WITH ROUND FORMING WIRE

BACKGROUND OF THE INVENTION

This invention relates to guidewires used in the placement of catheters in cardiovascular surgical procedures. More particularly, this invention relates to improvements in small diameter steerable guidewires.

A wide variety of guidewires are used for various medical purposes in the treatment of the human body. Among the more common uses is in blood vessels to guide a catheter to a site within the patient's blood vessel to perform the procedure for which the catheter is adapted. For example, guidewires, particularly small diameter steerable guidewires, perform an important function in percutanious translumenal coronary angioplasty ("PTCA").

Ideally, a guidewire should exhibit the following characteristics:

(1) a strong yet flexible tip;
(2) an easily formable tip, although not so formable that the guidewire takes a permanent set when the wire is bent over on itself during use in the body; and
(3) a tip that exhibits 1:1 tip torque response with no whipping.

Illustrative of such guidewires are those described in U.S. Pat. No. 4,545,390 to Leary and U.S. Pat. No. 4,538,622 to Samson et al. Each of the guidewires described in those patents has a tortionally rigid longitudinally flexible shaft and a flexible distal end that includes a radiopaque coil so that the physician can monitor fluoroscopically the position and advancement of the guidewire in the patient's blood vessel.

Many such existing guidewires provide a strong, flexible and formable tip. However, due to a non-symmetrical tip design including a flattened safety wire, such guidewires do not transmit torque 1:1. Where a guidewire does not provide 1:1 tip torque response, torsional energy is stored in the guidewire. At some point during arterial insertion the energy may be released causing the guidewire tip to "whip" or move in an unpredictable and uncontrolled manner. For a physician attempting to insert a guidewire in a tortuous anatomy, such unpredictable and uncontrolled behavior is unacceptable.

Accordingly, there is a need for a guidewire with a strong flexible tip that exhibits 1:1 tip torque response with no whipping.

SUMMARY OF THE INVENTION

With the foregoing in mind, it is an object of the invention to provide a guidewire that provides 1:1 tip torque response.

It is a further object of the invention to provide a guidewire with a strong yet flexible tip that exhibits no whipping.

The Guidewire With Rounded Forming Wire in accordance with the instant invention includes a helical coil and a core wire. The core wire extends into a lumen of the helical coil and has a proximal end of the helical coil fixedly attached thereto. The helical coil is secured at its proximal end and at a point along its length to the core wire by conventional brazed joints At least one round forming wire is fixedly attached to a distal region of the core wire and extends through the lumen of the helical coil. A rounded protrusion is provided at a distal end of the helical coil with the forming wire(s) and the helical coil fixedly attached thereto.

BRIEF DESCRIPTION OF THE DRAWINGS

The accompanying drawings, referred to herein and constituting a part hereof, illustrate preferred embodiments of the invention and, together with the description, serve to explain the principles of the invention, wherein:

FIG. 1 is a fragmented, sectional view of a guidewire in accordance with the invention;

FIG. 2 is a detailed view of the distal end of the guidewire of FIG. 1;

FIG. 5 is a fragmented, sectional view of a second alternative embodiment of a guidewire in accordance with the invention;

FIG. 6 is a detailed view of the distal end of the guidewire of FIG. 5;

FIG. 7 is a fragmented, sectional view of a third alternative embodiment of a guidewire in accordance with the invention; and FIG. 8 is a detailed view of the distal end of the guidewire of FIG. 7.

DETAILED DESCRIPTION OF THE DRAWINGS

Figure 3:
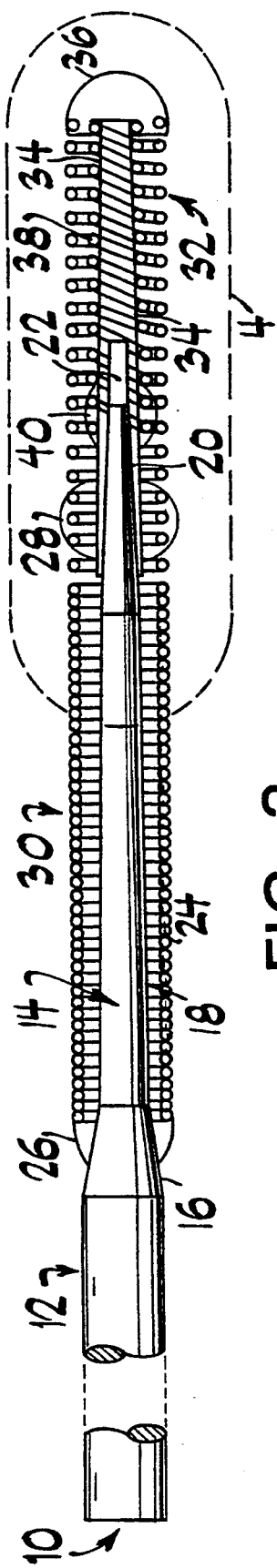
FIG. 3 is a fragmented, sectional view of a first alternative embodiment of a guidewire in accordance with the invention.

As shown in FIG. 1, the Guidewire With Round Forming Wire in accordance with the invention has a core wire 10 which is, e.g., a standard 0.0115 inch diameter Lumisilk ™ core wire as is used in guidewire products from C. R. Bard, Inc. The core wire is typically 49.011 inches (173.5 cm) in length and made of 304 V stainless steel.

The proximal region of core wire 10 includes larger diameter segment 12, approximately 0.0115 inches in diameter and 38.136 inches (135 cm) in length. The distal region of core wire 10 includes reduced diameter segment 14 which is approximately 10.876 inches (38.5 cm) in length and includes a first tapered portion 16 which is 2.825 inches (10 cm) in length and a primary barrel 18 which is 6.921 inches (24.5 cm) in length and 0.0057 inches in diameter followed by a second tapered portion 20 which is 0.989 inches (3.5 cm) in length and a distal barrel 22 which is 0.141 inches (0.5 cm) in length and 0.0019 inches in diameter.

A wound helical coil 24 which is 8.531 inches (30.2 cm) in length and 0.0114 inches in outside diameter and made from 0.0022 inch diameter 304 stainless steel wire is secured to the second tapered portion 20 of the core wire. The distal 0.565 inches (2 cm) of the helical coil may be plated with 230 micro inch gold to make the distal end of the guidewire radiopaque so that the physician can monitor fluoroscopically the position and advancement of the guidewire in the patient's blood vessel. Alternatively, the helical coil itself may be made of a radiopaque material, e.g., platinum/tungsten, gold/platinum, or gold/stainless steel. It may be appreciated that helical coil 24 has an outer dimension approximately equal to the outer dimension of larger diameter segment 12 of core wire 10.

The helical coil 24 abuts and is secured to the first tapered portion 16 of core wire 10 at the proximal end of helical coil 24 by a first conventional brazed joint 26 and at a point along the length of the helical coil to core wire 10 by a second conventional brazed joint 28 at a point approximately 0.480 inches (1.7 cm) from the end of distal barrel 22. It will be appreciated that the helical coil may also be secured to the core wire by welding, soldering, or in such other appropriate manner as is known in the art.

The helical coil 24 includes two sections: proximal to the second conventional brazed joint 28 is a stacked-coil section 30 which is 7.486 inches in length (26.5 cm) and 0.0104 inches in diameter and, distal to the second conventional brazed joint 28, an extended coil section 32 which is 1.045 inches in length (3.7 cm) and 0.0114 inches in diameter. The coil separation in the extended coil section begins approximately 0.339 inches (1.2 cm) distal of the second conventional brazed joint 28 and extends to the guidewire tip. The length of ten coils including separations is 0.032–0.037 inches.

It may be appreciated from FIG. 2 that distal barrel 22 of core wire 10 ends proximally of the end of helical coil 24. The core wire ends approximately 0.565 inches (2 cm) from the distal end of the helical coil. One to four round forming wires 34, 1.695 inches (6 cm) in length and 0.0015 inches in diameter, are brazed to core wire 10 by capturing the forming wires in the second conventional brazed joint 28, allowing at least 0.056 inches (2 mm) of forming wire to extend proximal to the second conventional brazed joint 28. The forming wires 34 are preferably a 304 V HiTen stainless steel. Although a single forming wire may be used, a symmetrical tip arrangement is preferable making two or more forming wires symmetrically arranged around the reduced diameter segment 14 of core wire 10 desirable.

The distal ends of helical coil 24 and forming wires 34 are secured to a rounded protrusion 36 formed at the end of the guidewire. The rounded protrusion may be formed by various methods as are know in the art including melting the distal ends of the helical coil and forming wires by the use of a welder as disclosed in U.S. Pat. No. 4,811,743 to Stevens.

The guidewire surface may be covered with a protective lubricious coating prior to use. One such coating includes a urethane dispersion, a siloxane dispersion, polyfunctional aziridine and distilled water as disclosed in U.S. Pat. No. 5,026,607 to Klezulas.

Figure 4:
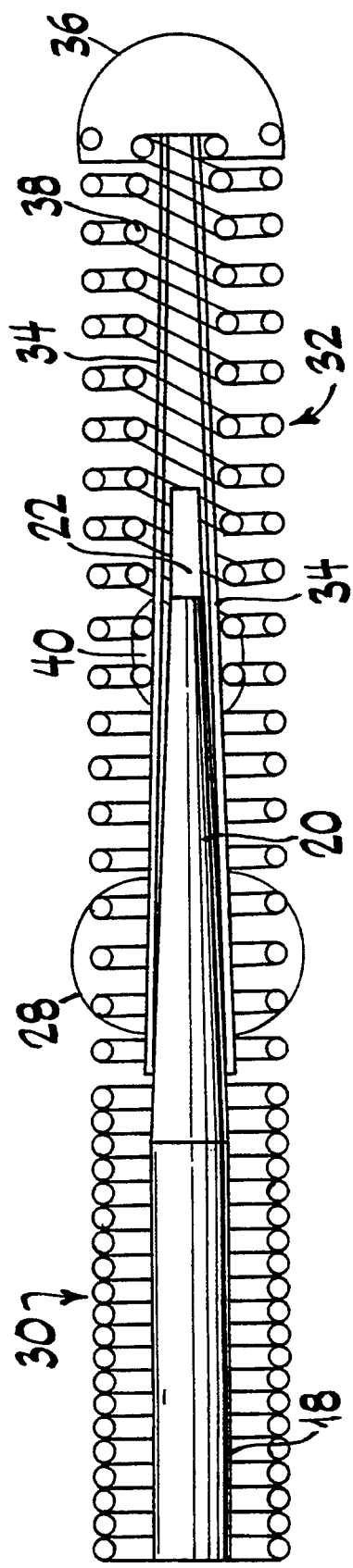
FIG. 4 is a detailed view of the distal end of the guidewire of FIG. 3.

In FIGS. 3 and 4 are shown a first alternative embodiment of the guidewire in accordance with the invention wherein similar reference numerals are applied to similar features. In this embodiment, an inner coil 38 is provided to increase the radiopacity of the guidewire tip as an aid to fluoroscopic monitoring of the guidewire in use.

A helically wound inner coil 38 is provided which is formed of 0.0025 inch diameter Au-Pt wire. The proximal end of the inner coil 38, positioned within helical coil 24, is secured to reduced diameter segment 14 of core wire 10 by a third conventional brazed joint 40 and the distal end of the inner coil 38 is secured along with the distal end of helical coil 24 and forming wires 34 to rounded protrusion 36 positioned at the end of the guidewire.

It may be appreciated from FIG. 4 that the forming wires 34 may be secured to the reduced diameter segment 14 of core wire 10 by both second conventional brazed joint 28 and third conventional brazed joint 40. Including the forming wires in both brazed joints during the manufacturing process insures a solid connection of the forming wires to the core wire.

In FIGS. 5 and 6 is shown a second alternative embodiment of the guidewire in accordance with the invention wherein similar reference numerals are again applied to similar features. In this embodiment, an alternative core wire 10 as is used, e.g., in Phantom ™ guidewire products of C. R. Bard, Inc. The distal barrel 22 (of FIG. 1) of core wire 10 is here extended into a round straight 0.0015 inch diameter tip wire 42 approximately 0,424 inches (1.5 cm) in length. The tip wire 42 may be connected at the rounded protrusion 36 created by a welder at the distal ends of the inner and helical coils.

In FIGS. 7 and 8, is shown a third alternative embodiment of the guidewire in accordance with the invention wherein similar reference numerals are again applied to similar features. The distal barrel 22 (of FIG. 1) of core wire 10 is here again extended into a round straight 0.0015 inch diameter tip wire 42. The tip wire 42 is connected at the rounded protrusion 36 created by a welder to the distal ends of the helical and inner coils, 24, 38. One to four round forming wires 34 (as described with respect to FIG. 1) are secured to the reduced diameter segment 14 of the core wire 10 and connected to the rounded protrusion 36. The arrangement of FIGS. 7 and 8 provides a guidewire with particular added strength and torque in the guidewire tip resulting from the combination of the one to four round forming wires with the tip wire.

It may be appreciated that the tip of each of the above-described embodiments is strong yet flexible and easy to form. The structure of the guidewire, however, is not so formable that the guidewire takes a permanent set when bent over on itself. In contrast, a prior art guidewire using a flattened safety wire as a ribbon may facilitate the shaping of the guidewire coil but the guidewire coil takes a permanent set when bent over on itself.

While the invention has been described in its preferred embodiments, it is to be understood that the words which have been used are words of description, rather than limitation, and that changes may be made within the purview of the appended claims without departing from the true scope and spirit of the invention in its broader aspects.

What is claimed:

1. A guidewire, comprising:
   a helical coil having a proximal end, a distal end, and a lumen;
   a core wire having a distal region extending into a lumen of said helical coil and having a proximal end of said helical coil fixedly attached to said core wire;
   a plurality of cylindrical round forming wires fixedly attached to said distal region of said core wire and extending through said lumen of said helical coil; and
   a protrusion provided at said distal end of said helical coil with said plurality of round cylindrical forming wires and said helical coil fixedly attached thereto;
   whereby said plurality of round cylindrical forming wires provides both increased tensile strength and decreased stiffness to the guidewire.

2. A guidewire in accordance with claim 1, wherein said plurality of round forming wires are fixedly attached to said core wire by a brazed joint.

3. A guidewire in accordance with claim 1, wherein said protrusion is formed by melting said helical coil and said plurality of round forming wires into a rounded tip.

4. A guidewire in accordance with claim 1, wherein said helical coil is fixedly attached to said core wire by at least one brazed joint.

5. A guidewire in accordance with claim 1, wherein said helical coil is fixedly attached to said core wire at a tapered section thereof.

6. A guidewire in accordance with claim 5, wherein said helical coil is fixedly attached to said core wire by a brazed joint at a proximal end thereof.

7. A guidewire in accordance with claim 1, wherein individual coils of said helical coil are expanded along a partial length thereof.

* * * * *